(12) United States Patent
Guenst

(10) Patent No.: US 7,063,693 B2
(45) Date of Patent: *Jun. 20, 2006

(54) METHODS AND TOOLS FOR ACCESSING AN ANATOMIC SPACE

(75) Inventor: Gary W. Guenst, Collegeville, PA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/902,314

(22) Filed: Jul. 29, 2004

(65) Prior Publication Data

US 2004/0267303 A1 Dec. 30, 2004

Related U.S. Application Data

(63) Continuation of application No. 10/342,960, filed on Jan. 15, 2003, now Pat. No. 6,786,898.

(51) Int. Cl.
*A61B 17/00* (2006.01)

(52) U.S. Cl. .......................... 606/1; 604/115; 600/114; 600/37

(58) Field of Classification Search ................ 604/115, 604/117, 93.01, 164.4, 506, 500, 176, 902, 604/264, 96.01, 528, 908; 606/205, 167, 606/108; 600/509, 114, 115, 201, 37, 104, 600/156

See application file for complete search history.

(56) References Cited

U.S. PATENT DOCUMENTS

| | | | |
|---|---|---|---|
| 4,662,376 A | 5/1987 | Belanger | 606/125 |
| 4,723,940 A | 2/1988 | Wiegerinck | 604/115 |
| 4,991,578 A | 2/1991 | Cohen | 128/419 D |
| 5,071,428 A | 12/1991 | Chin et al. | 606/184 |
| 5,336,252 A | 8/1994 | Cohen | 607/119 |
| 5,452,733 A | 9/1995 | Sterman et al. | 128/898 |
| 5,464,447 A | 11/1995 | Fogarty et al. | 607/129 |
| 5,630,795 A * | 5/1997 | Kuramoto et al. | 604/30 |
| 5,716,392 A | 2/1998 | Bourgeois et al. | 607/132 |
| 5,827,216 A | 10/1998 | Igo et al. | 604/21 |
| 5,868,770 A | 2/1999 | Rygaard | 606/167 |
| 5,875,782 A | 3/1999 | Ferrari et al. | 128/898 |
| 5,972,013 A | 10/1999 | Schmidt | 606/185 |
| 6,059,719 A | 5/2000 | Yamamoto et al. | 600/127 |
| 6,080,175 A | 6/2000 | Hogendijk | 606/185 |
| 6,156,009 A | 12/2000 | Grabek | 604/117 |

(Continued)

*Primary Examiner*—Beverly M. Flanagan
(74) *Attorney, Agent, or Firm*—Tom Berry; Jeffrey J. Hohenshell

(57) ABSTRACT

A tubular access sleeve and suction tool for accessing an anatomic surface or anatomic space and particularly the pericardium to access pericardial space and the epicardial surface of the heart in a minimally invasive manner are disclosed. A suction tool trunk extending through a suction tool lumen of the sleeve is coupled to suction pads at the ends elongated support arms. The suction pads can be retracted into a sleeve working lumen during advancement of the access sleeve through a passage and deployed from the tubular access sleeve lumen and disposed against the an outer tissue layer. Suction can be applied through suction tool lumens to suction ports of the suction pads that fix to the outer tissue layer so as to tension the outer tissue layer and/or pull the outer tissue layer away from an inner tissue layer so that the anatomic space can be accessed by instruments introduced through the working lumen to penetrate the outer tissue layer.

16 Claims, 5 Drawing Sheets

U.S. PATENT DOCUMENTS

| | | |
|---|---|---|
| 6,231,518 B1 | 5/2001 | Grabek et al. .............. 600/508 |
| 6,332,468 B1 | 12/2001 | Benetti ....................... 128/898 |
| 6,394,948 B1 | 5/2002 | Borst et al. ................... 600/37 |
| 6,423,051 B1 | 7/2002 | Kaplan et al. .............. 604/506 |
| 6,464,630 B1 | 10/2002 | Borst et al. ................... 600/37 |
| 6,786,898 B1 * | 9/2004 | Guenst .......................... 606/1 |

* cited by examiner

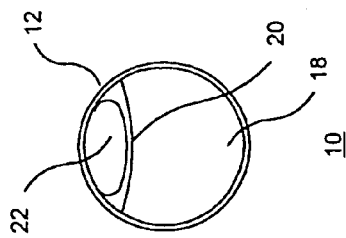
FIG. 3
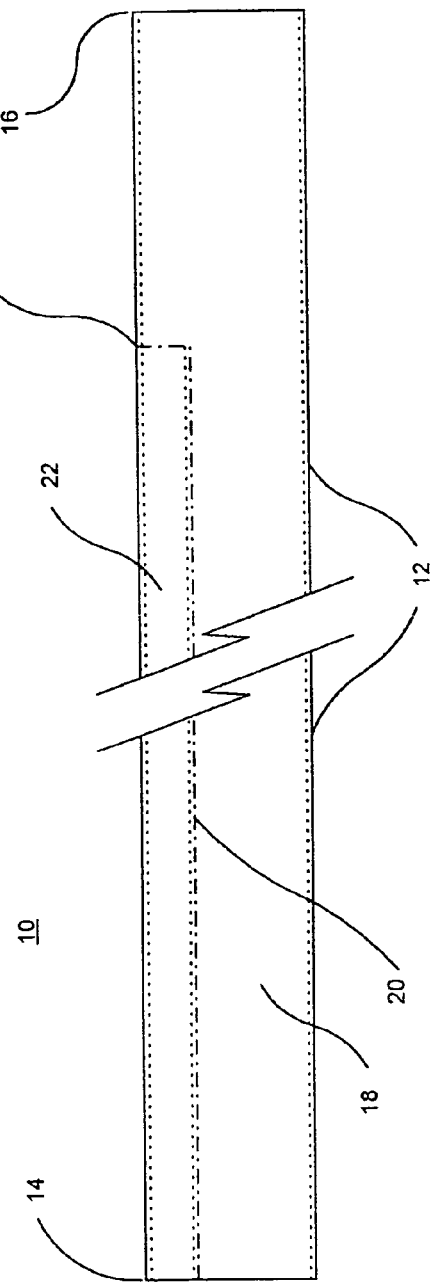
FIG. 2
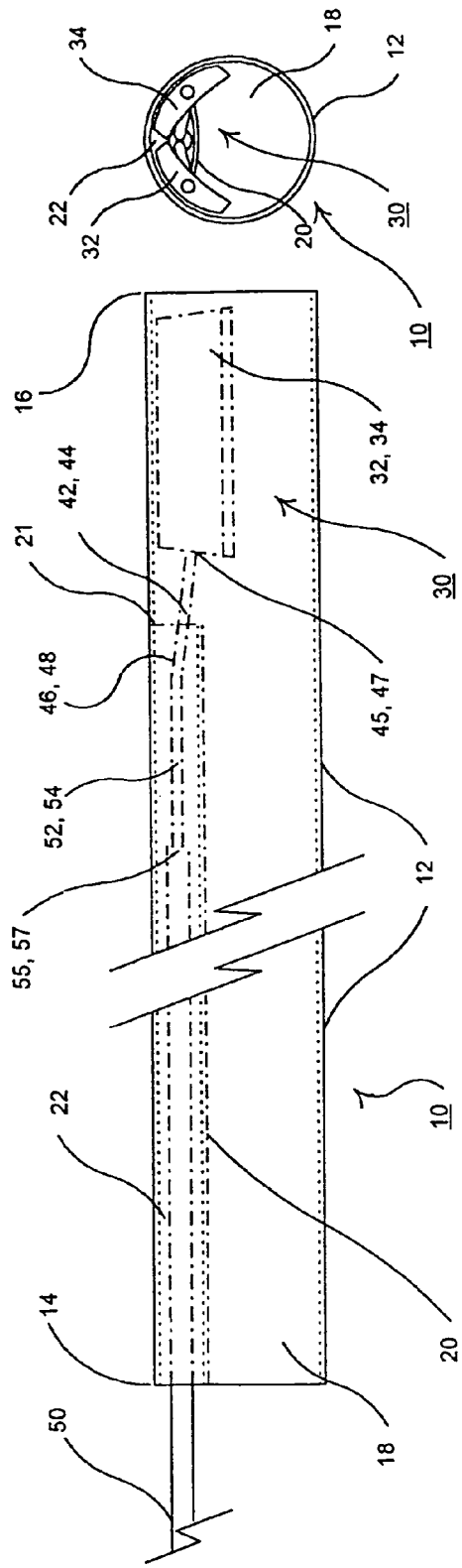
FIG. 7
FIG. 6

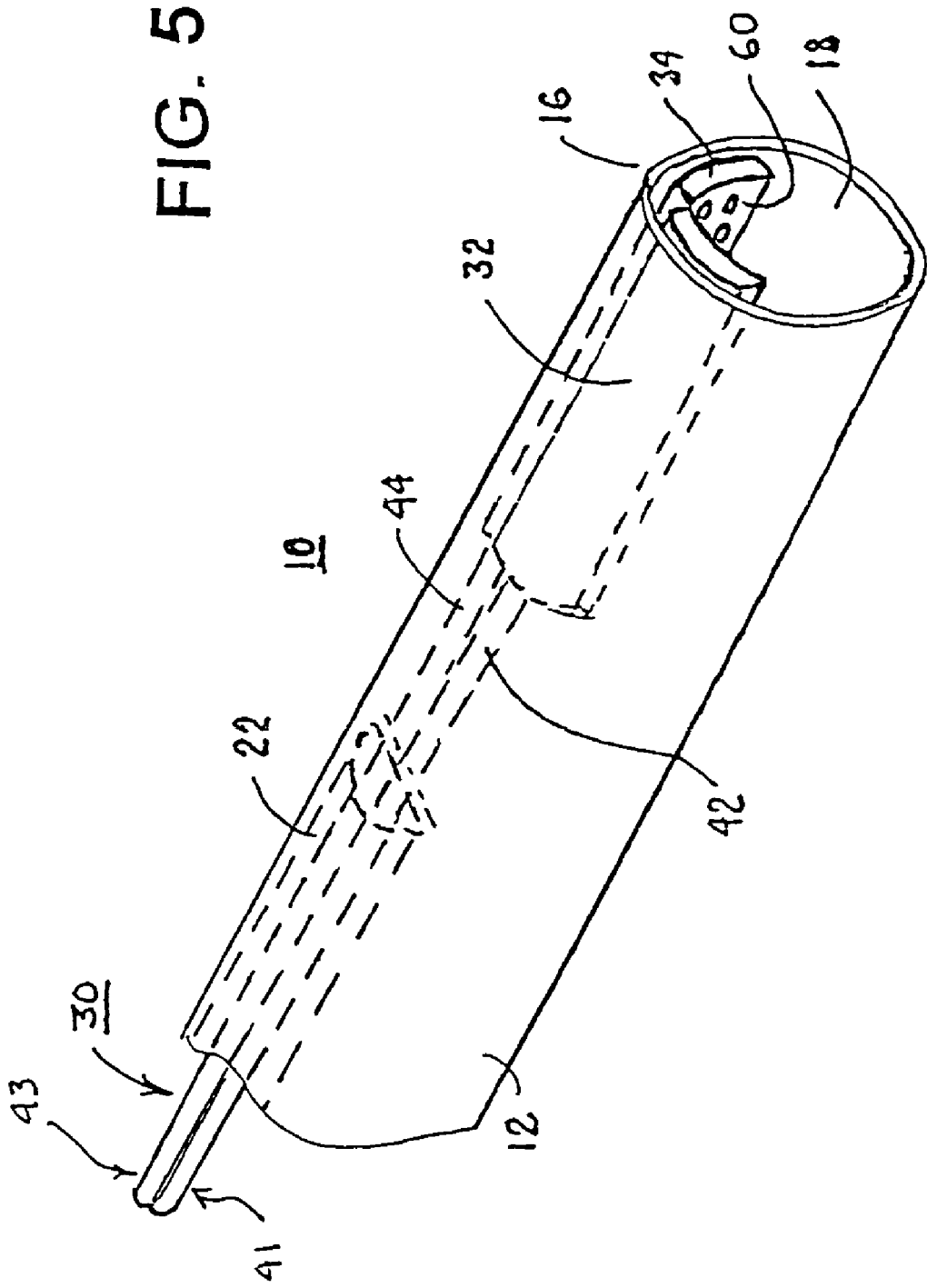

METHODS AND TOOLS FOR ACCESSING AN ANATOMIC SPACE

CROSS-REFERENCE TO RELATED APPLICATIONS

This application is a continuation of U.S. Ser. No. 10/342,960, filed Jan. 15, 2003, now issued as U.S. Pat. No. 6,786,898.

FIELD OF THE INVENTION

The present invention pertains to medical devices and methods for accessing an anatomic surface, muscle layer, vessel or anatomic space of the body and particularly for entering the pericardium to access pericardial space and the epicardial surface of the heart in a minimally invasive manner.

BACKGROUND OF THE INVENTION

The human heart wall consists of an inner layer of simple squamous epithelium, referred to as the endocardium, overlying a variably thick heart muscle or myocardium and is enveloped within a multi-layer tissue structure referred to as the pericardium. The innermost layer of the pericardium, referred to as the visceral pericardium or epicardium, clothes the myocardium. The epicardium reflects outward at the origin of the aortic arch to form an outer tissue layer, referred to as the parietal pericardium, which is spaced from and forms an enclosed sac extending around the visceral pericardium of the ventricles and atria. An outermost layer of the pericardium, referred to as the fibrous pericardium, attaches the parietal pericardium to the sternum, the great vessels and the diaphragm so that the heart is confined within the middle mediastinum. Normally, the visceral pericardium and parietal pericardium lie in close contact with each other and are separated only by a thin layer of a serous pericardial fluid that enables friction free movement of the heart within the sac. The space (really more of a potential space) between the visceral and parietal pericardia is referred to as the pericardial space. In common parlance, the visceral pericardium is usually referred to as the epicardium, and epicardium will be used hereafter. Similarly, the parietal pericardium is usually referred to as the pericardium, and pericardium will be used hereafter in reference to parietal pericardium.

It is frequently medically necessary to access the pericardial space to treat an injury, infection, disease or defect of the heart, e.g., an occluded coronary artery, a defective heart valve, aberrant electrical pathways causing tachyarrhythmias, bacterial infections, to provide cardiac resynchronization therapy, or to place epicardial pacing or cardioversion/defibrillation electrodes against the epicardium or into the myocardium at selected sites. It is necessary in these procedures to surgically expose and cut through the pericardium to obtain access to the pericardial space.

Highly invasive surgical techniques, referred to as a median sternotomy (open-chest surgical exposure) or a thoracotomy, have been typically employed to provide the surgeon access to the pericardial space and the heart. A median sternotomy incision begins just below the sternal notch and extends slightly below the xyphoid process. A sternal retractor is used to separate the sternal edges for optimal exposure of the heart. Hemostasis of the sternal edges is typically obtained using electrocautery with a ball-tip electrode and a thin layer of bone wax.

The open chest procedure involves making a 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire hooks to keep the severed sternum together. Such surgery often carries additional complications such as instability of the sternum, post-operative bleeding, and mediastinal infection. The thoracic muscle and ribs are also severely traumatized, and the healing process results in an unattractive scar. Post-operatively, most patients endure significant pain and must forego work or strenuous activity for a long recovery period.

Many minimally invasive surgical techniques and devices have been introduced in order to reduce the risk of morbidity, expense, trauma, patient mortality, infection, and other complications associated with open-chest cardiac surgery. Less traumatic limited open chest techniques using an abdominal (sub-xyphoid) approach or, alternatively, a "Chamberlain" incision (an approximately 8 cm incision at the sternocostal junction), have been developed to lessen the operating area and the associated complications. In recent years, a growing number of surgeons have begun performing coronary artery bypass graft (CABG) procedures using minimally invasive direct coronary artery bypass grafting (MIDCAB) surgical techniques and devices. Using the MIDCAB method, the heart typically is accessed through a mini-thoracotomy (i.e., a 6 to 8 cm incision in the patient's chest) that avoids the sternal splitting incision of conventional cardiac surgery. A MIDCAB technique for performing a CABG procedure is described in U.S. Pat. No. 5,875,782, for example.

Other minimally invasive, percutaneous, coronary surgical procedures have been advanced that employ multiple small trans-thoracic incisions to and through the pericardium, instruments advanced through ports inserted in the incisions, and a thoracoscope to view the accessed cardiac site while the procedure is performed as shown, for example, in U.S. Pat. Nos. 6,332,468, 5,464,447, and 5,716,392. Surgical trocars having a diameter of about 3 mm to 15 mm are fitted into lumens of tubular trocar sleeves, cannulae or ports, and the assemblies are inserted into skin incisions. The trocar tip is advanced to puncture the abdomen or chest to reach the pericardium, and the trocar is then withdrawn leaving the sleeve or port in place. Surgical instruments and other devices such as fiber optic thoracoscopes can be inserted into the body cavity through the sleeve or port lumens. As stated in the '468 patent, instruments advanced through trocars can include electrosurgical tools, graspers, forceps, scalpels, electrocauteries, clip appliers, scissors, etc.

In such procedures, the surgeon can stop the heart by utilizing a series of internal catheters to stop blood flow through the aorta and to administer cardioplegia solution. The endoscopic approach utilizes groin cannulation to establish cardio-pulmonary bypass (CPB) and an intraaortic balloon catheter that functions as an internal aortic clamp by means of an expandable balloon at its distal end used to occlude blood flow in the ascending aorta. A full description of an example of one preferred endoscopic technique is found in U.S. Pat. No. 5,452,733, for example.

However, recently developed, beating heart procedures eliminate the need for any form of CPB, the extensive surgical procedures necessary to connect the patient to a CPB machine, and to stop the heart. These beating heart procedures can be performed on a heart exposed in a full or limited thoracotomy or accessed percutaneously as described particularly in reference to FIG. 19 in U.S. Pat. No. 6,394,948, for example.

In such percutaneous procedures, the epicardium of the beating or stopped heart is exposed to view typically by use of grasping and cutting instruments inserted through one port to cut through the pericardium surrounding the heart while the area is viewed through the thoracoscope or endoscope inserted through another port. The thoracoscopic approach typically requires the placement of a chest tube and admission to the hospital for the initial 1–2 postoperative days.

Therefore, much effort has been expended to develop medical devices and techniques to access the pericardial space employing such minimally invasive percutaneous procedures. One difficulty has been that normally the pericardial space is so small or thin that it is difficult to penetrate the pericardium using miniaturized instruments capable of being introduced through a port to the site without also puncturing the underling epicardium and thereby, damaging the myocardium or a coronary vessel. Proliferative adhesions occur between the pericardium and the epicardium in diseased hearts and hamper access to the pericardial space employing such minimally invasive percutaneous procedures. The simple percutaneous approach can be used to penetrate the pericardium to drain a large pericardial effusion, i.e., an accumulation of too much fluid in the pericardial space that widens the pericardial space. A spinal needle (18–20 gauge) and stylet occluding the needle lumen are advanced incrementally in a superior/posterior fashion through a small (2–4 mm) cutaneous incision between the xyphoid and costal cartilage. Periodically, the stylet is removed, and fluid aspiration is attempted through the needle lumen. The advancement is halted when fluid is successfully aspirated, and the pericardial effusion is then relieved.

Methods and apparatus for accessing the pericardial space for the insertion of implantable defibrillation leads are disclosed in U.S. Pat. Nos. 5,071,428 and 6,156,009, wherein a forceps device is used to grip the pericardium and pull it outward to form a "tent". In the '428 patent, a scissors or scalpel is introduced to cut the pericardium (pericardiotomy) under direct vision through a sub-xyphoid surgical incision. The forceps device disclosed in the '009 patent incorporates a mechanism for introducing electrical leads or guidewires through the outwardly displaced pericardium. It is difficult to introduce and use the forceps through the narrow lumen of a port or sleeve, particularly if the pericardial fluid is under pressure that makes the pericardium taut like an inflated balloon.

Further methods and apparatus for accessing the pericardial space for the insertion of devices or drugs are disclosed in U.S. Pat. No. 6,423,051, wherein an access tube having a device access lumen is provided with a plurality of hooks in the tube distal end that can be used to hook into the pericardium to enable the lifting and "tenting" of the pericardium. A cutting instrument or sharpened tip guidewire or the like can be advanced through the device access lumen to perforate the pericardium.

Other methods and apparatus that are introduced through percutaneously placed ports or directly through small transthoracic incisions for accessing the pericardial space employ suction devices to grip the pericardium or epicardium as disclosed, for example, in U.S. Pat. Nos. 4,991,578, 5,336, 252, 5,827,216, 5,868,770, 5,972,013, 6,080,175, and 6,231, 518 and the above-referenced '948 patent. The suction device is configured like a catheter or tube having a single suction tool lumen and typically having a further instrument delivery lumen. The suction tool lumen terminates in a single suction tool lumen end opening through the device distal end in the '578, '252, '175, '770, and '013 patents and through the device sidewall in the '216 and '518 patents. Certain of these patents recite that the applied suction draws a "bleb," i.e., a locally expanded region of the pericardium, into the suction tool lumen or a suction chamber at the device distal end. A needle can then be advanced into the bleb and used to draw off fluids or deliver drugs into the pericardial space, or the like. In addition, it is suggested in these patents that treatment devices including catheters, guidewires, and electrodes, e.g., defibrillation electrodes, can be advanced into the pericardial space through a device introduction lumen for a variety of reasons. Although theoretically plausible, the ability to reliably maintain a vacuum seal against the pericardium when such treatment devices are advanced can be problematic.

For these reasons, it would be desirable to provide additional and improved methods and apparatus for the minimally invasive access to a patient's pericardial space (or other anatomic space). The methods and devices should be suitable for a wide variety of minimally invasive approaches to the pericardium, including at least intercostal/transthoracic and subxiphoid approaches, and the like. The methods and devices should further provide for secure and stable capture of the pericardium and permit the opening of a large space or volume between the pericardium and epicardium. Such access methods and apparatus should be useful for a wide variety of procedures to be performed in the pericardial space, including fluid withdrawal, drug delivery, diagnostic and therapeutic electrophysiology procedures, pacemaker lead implantation, defibrillator lead placement, transmyocardial revascularization, transmyocardial revascularization with drug delivery, placement of the left ventricular assist devices, placement of the arterial bypass graphs, in situ bypass, i.e., coronary artery-venous fistulae, placement of drug delivery depots, closure of the left arterial appendage, and the like. At least some of these objectives will be met by the invention described herein.

SUMMARY OF THE INVENTION

One aspect of the present invention provides methods, apparatus, and kits for accessing an anatomic space between an inner tissue layer and an outer tissue layer. The phrase "anatomic space" is meant to include any natural, potential, or created space or cavity within a patient's body where it may be desirable to gain access for surgical, diagnostic, therapeutic, lead delivery, visualization, or any other purpose. The inner tissue layer may consist of a membrane, a capsule or the adventia, muscularis and endothelial layers of a hollow organ or vessel. The methods, apparatus, and kits are particularly useful for minimally invasive access procedures, but could also be used for accessing internal anatomic spaces where initial access to the outer tissue layer is achieved via open surgical procedures. The present invention will be particularly useful for accessing a patient's pericardial space between the epicardium and pericardium for performing a wide variety of procedures, generally as set forth above. Other internal organs that may be accessed include the intestines, fallopian tubes, gall bladder, kidneys, and the like.

Apparatus and methods according to the present invention for accessing such an anatomic space utilize an elongated tubular access sleeve adapted to be advanced through a small incision to dispose an access sleeve distal end in operative relation to the outer tissue layer. An access sleeve working lumen of the tubular access sleeve of the present invention can be used to introduce an instrument or material to the outer tissue layer. The instrument can be a cutting tool for perforating and making an incision through the outer tissue layer so that further instruments or implantable medical devices or drugs or diagnostic agents or the like can be introduced through the sleeve lumen into the anatomic space.

The modified tubular access sleeve incorporates or accommodates a suction tool comprising at least two suction pads at the ends of at least two elongated arms that can be retracted into the tubular access sleeve during introduction and advancement of the tubular access sleeve distal end into operative relation to the outer tissue layer. Then, the suction pads can be advanced from the working lumen and deployed out of the tubular access sleeve lumen and disposed against the outer tissue layer. Suction can be applied through suction tool lumens to suction ports of the suction pads that fix to the outer tissue layer so as to tension the outer tissue layer and/or pull the outer tissue layer away from the inner tissue layer and/or stabilize the outer tissue layer and/or track any movements of the outer tissue layer.

The suction pads advantageously facilitated cutting into or through the outer tissue layer with a cutting instrument. Initially, suction is applied so that the suction pads grasp the surface of the outer tissue layer. A cutting instrument or tool can then be introduced through the working lumen to dispose a cutting element at the tissue surface. The suction pads are also spread apart so that the tissue surface is tensioned during cutting. In this way, the perforation or hole that is cut is widened by the applied tension. The widened hole can then be maintained for passage of further devices into or through the hole.

In a preferred embodiment, a pair of elongated support arms each support an elongated suction pad comprising a plurality of suction ports and a suction manifold connecting the suction ports to a suction tool lumen of the support arm. Suction applied through the suction ports grasps tissue. Each suction pad is coupled to the distal end of the support arm optionally through a flexible wrist. Each support arm comprises a distal forearm extending from the wrist to a flexible elbow and a proximal or upper arm extending from the elbow to a flexible shoulder joint with a common proximal suction tool trunk.

The proximal suction tool trunk extends proximally through an access sleeve suction tool lumen of the tubular access sleeve to a suction fitting at the proximal end of the trunk that can be coupled to an available surgical operating room vacuum source.

The trunk and support arms can be drawn proximally into the access sleeve suction tool lumen to dispose the suction pads within a distal portion of the working lumen during surgical insertion or withdrawal of the tubular access sleeve from the patient's body. The trunk and support arms can be advanced distally through the access sleeve suction tool lumen to extend the support arms and suction pads from the distal end opening of the working lumen.

Each support arm is formed of a flexible tube that has preformed bends at the wrist, elbows, and shoulders that, when unrestrained, dispose the suction pads apart from one another a distance so that the suction pads can cooperatively grasp the outer tissue layer at separated apart locations generally so that the outer tissue layer between the suction pads can be operatively accessed through the working lumen. The preformed bends at the wrists, elbows and shoulders can be overcome to dispose the arms parallel to one another when drawn proximally into the access sleeve suction tool lumen. The elongated suction pads are drawn together and aligned axially with the working lumen so that the suction pads can be drawn into the distal segment of the working lumen.

Due to their redundancy, the suction ports of the suction pads provide more robust fixation to the outer tissue layer than a single large area suction port. At least some of the suction ports readily engage the tissue surface under low suction force to enable lifting of the outer tissue layer or tracking movement of the outer tissue layer. Engagement of tissue surface areas by all of the suction ports is not necessary. Similarly, the loss of engagement of some of suction ports with the tissue surface areas does not result in complete loss of engagement as is the case when an edge of a single large suction port releases from the tissue surface of the outer tissue layer.

A cutting instrument, e.g., a knife, a needle, a stiff guidewire tip, an electrosurgical cutting tool, surgical scissors or other piercing or cutting tool, can then be introduced through the working lumen to perforate the outer tissue layer and form an access hole or perforation there through creating access into the anatomic space while the access tube stabilizes the outer tissue layer. Advantageously, there is no suction applied through the working lumen that is necessary to maintain the attachment to the outer tissue layer while it is being perforated or other instruments are advanced through the perforation. The fixation of the outer tissue layer is not lost when the outer tissue layer is perforated. Moreover, it is simpler to advance instruments through the working lumen from a proximal lumen end opening that is exposed to the atmosphere.

The methods, apparatus and kits of the present invention can advantageously be used to access the pericardial space between the pericardium and epicardium. In a still further aspect of the present invention, various devices are introduced into the pericardial space for temporary treatment of the heart or pericardial space or to complete a surgical procedure or for permanent implantation against the epicardium or within the pericardial space or within the myocardium or within a coronary vein or artery.

The tubular access sleeve can be circular or oval or have any other desirable cross-section shape. The tubular access sleeve can be straight, curved or formed with a bend or formed of a bendable material to be shaped by the user. The tubular access sleeve and the suction tool are formed of non-conductive materials to minimize electrical hazards. The tubular access sleeve and the suction tool can be provided in a range of diameters and lengths to function as described herein to access any desired site in the body of adult and pediatric patients.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 2 is a side view of a tubular access sleeve of the present invention;

FIG. 3 is an end view of the tubular access sleeve of FIG. 2;

FIG. 5 is a perspective view of the distal segment of the tubular access sleeve of FIG. 2 loaded with the suction tool of FIG. 4 with the suction pads disposed within a distal section of the working lumen of the access sleeve;

FIG. 6 is a side view of the tubular access sleeve of FIG. 2 loaded with the suction tool of FIG. 4 with the suction pads disposed within the distal section of the working lumen of the access sleeve;

FIG. 7 is an end view of the tubular access sleeve of FIG. 2 loaded with the suction tool of FIG. 4 with the suction pads disposed within the distal section of the working lumen of the access sleeve.

DETAILED DESCRIPTION OF THE PREFERRED EMBODIMENTS

In the following detailed description, references are made to illustrative embodiments of methods and apparatus for carrying out the invention. It is understood that other embodiments can be utilized without departing from the scope of the invention. Preferred methods and apparatus are described for accessing the pericardial space between the epicardium and the pericardium as an example of accessing an anatomic space between an outer tissue layer and an inner tissue layer.

The access to the pericardial space in accordance with the present invention facilitates the performance of a number of ancillary procedures. For example, the procedures include introducing and locating the distal end of a catheter or guidewire or an electrode of a cardiac ablation catheter or a pacing lead or a cardioversion/defibrillation lead within the pericardial space and attached to the epicardium or myocardium. Other possible procedures include performing a coronary artery anastomosis in a thoracoscopic CABG procedure, replacing a defective heart valve, ablating aberrant electrical pathways in the atria to alleviate atrial tachyarrhythmias, introducing drugs or anti-bacterial agents into the pericardial space, relieving pericardial fluid pressure or providing cardiac resynchronization therapy.

The passage is typically formed employing one-piece rods or trocars of prescribed diameters and lengths that are advanced through body tissue to form the passage and then removed so that other instruments can be advanced through the passage. The passage can also be formed employing two piece trocars that comprise a tubular outer sleeve, sometimes referred to as a port or cannula or at times as the tubular access sleeve itself, having a working lumen extending between lumen end openings at the sleeve proximal end and sleeve distal end, and an inner puncture core or rod that fits within the working lumen. The inner puncture rod typically has a tissue penetrating distal end that extends distally from the sleeve distal end when the inner puncture rod is fitted into the working lumen for use. The two-piece trocar can be assembled and advanced as a unit through body tissue, and the inner puncture rod then removed leaving the tubular access sleeve in place to maintain a fixed diameter passage through the tissue for use by other instruments.

The preferred embodiments of the present invention can be incorporated into a tubular access sleeve of such a two-piece trocar or can be inserted through the trocar sleeve lumen after removal of the inner puncture rod or inserted through a passage formed through body tissue by a one-piece trocar removed from the passageway. In either case, the tubular access sleeve of the present invention extends from a skin incision to an internal body organ or other structure of interest. The tubular access sleeve of the present invention is therefore elongated, tubular, and axially stiff.

Figure 1:
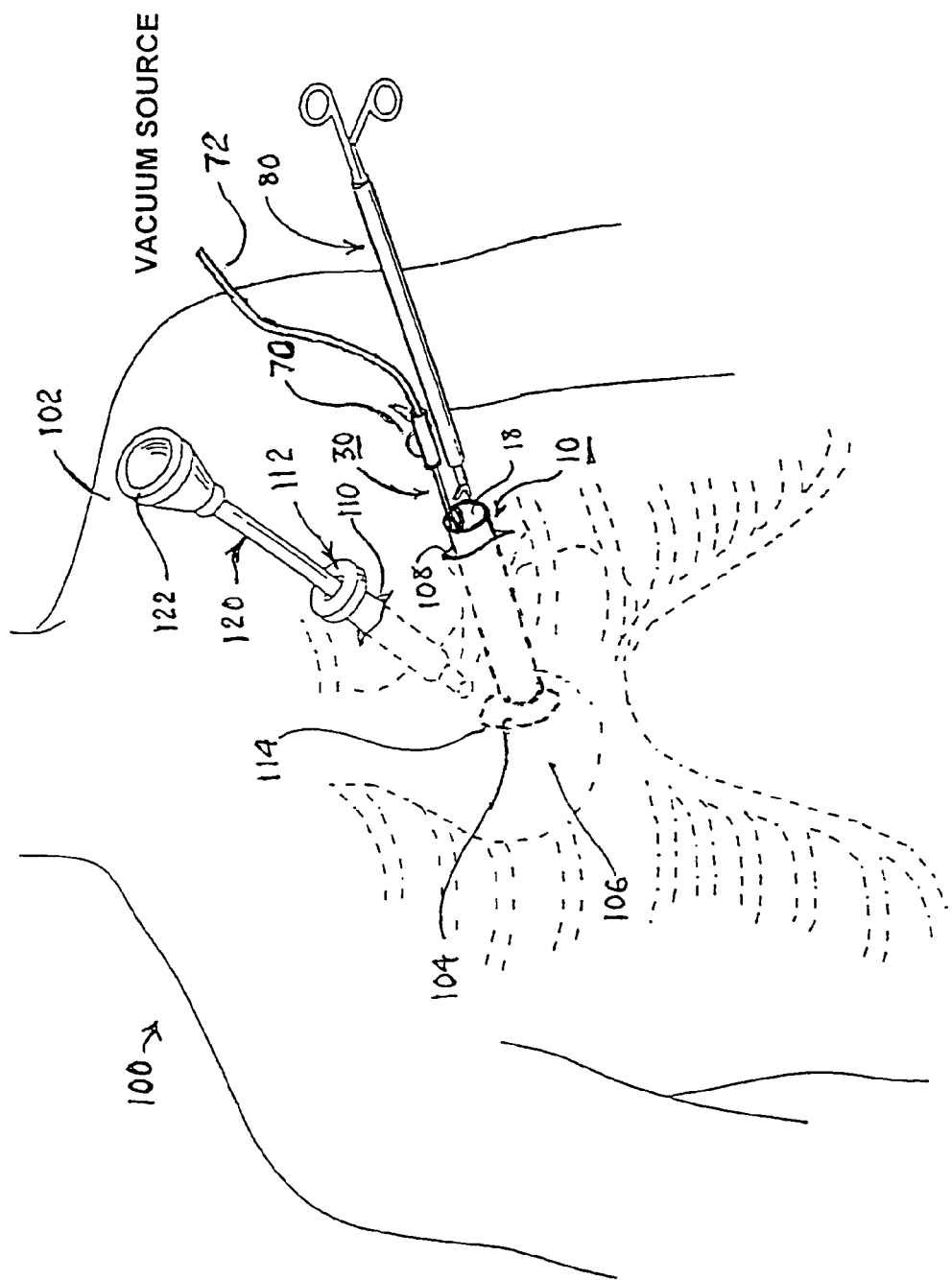
FIG. 1 is an illustration of the preparation of a patient for accessing the pericardial space through the use of a tubular access sleeve and suction tool of the present invention.

For example, FIG. 1 illustrates the placement of instruments through the chest wall of a patient 100 for observation and accessing the pericardial space through an incision in the pericardium 106 exposing the pericardium of the heart 104 to perform any of the ancillary procedures listed above. The patient 100 is placed under general anesthesia, and the patient's left lung is deflated if necessary, using conventional techniques. The patient 100 is placed in a lateral decubitus position on his right side, and small percutaneous incisions are to be made in the skin 102 through the chest wall for the receipt of surgical instruments. As used herein, the term "percutaneous" refers to any penetration through the skin of the patient, whether in the form of a small cut, incision, hole, cannula, tubular access sleeve or port or the like, that is preferably made in an interstitial space between the ribs of the patient 100.

A tubular access sleeve 10 in accordance with the present invention is shown left in place in a first passage 108 that is made as described above in the chest wall of patient 100 between the patient's 2nd rib and 6th rib, for example. The selection of the exact location of the first passage 108 is dependent upon a patient's particular anatomy. A further conventional tubular access sleeve 112 is shown left in place in a second passage 110 that is made as described above in the chest wall of patient 100.

Typically, the patient's left lung is deflated to allow unobstructed observation of the pericardium 106 employing a thoracoscope 120 inserted through a lumen of a tubular access sleeve 112. Frequently, the deflation is accomplished by use of a double lumen endotracheal tube that is inserted into the trachea, and independent ventilation of the right, left or both lungs can be selected. The left lung will collapse for visualization of the structures of the left hemi-sternum when ventilation of the left lung is halted and the left thoracic negative pressure is relieved through a lumen of the tubular access sleeve 112 or a further access sleeve to atmospheric pressure. After deflation, the thoracic cavity is suffused with a gas, e.g., carbon monoxide, introduced through a lumen of the tubular access sleeve 112 or the further access sleeve to pressurize the cavity to keep it open and sterile. The pressurized gas keeps the deflated lung away from the left heart so that the left heart can be viewed and accessed and provides a working space for the manipulation of the tools of the present invention. It will be understood that the access sleeve lumens must be sealed with seals about instruments introduced through the lumens to maintain the pressurization.

A thoracoscope 120 can then inserted into the lumen of the tubular access sleeve 112 to permit observation by a surgeon directly through an eyepiece 122 or indirectly through incorporation of a miniaturized image capture device, e.g., a digital camera, at the distal end of the thoracoscope 120 or optically coupled to the eyepiece 122 that is in turn coupled to an external video monitor (not shown). The thoracoscope 120 also incorporates a light source for illuminating the cavity with visible light so that the epicardial surface can be seen directly or indirectly. The depicted thoracoscope 120 is used to directly visualize the thoracic cavity and obtain a left lateral view of the pericardial sac or pericardium 106 over the heart 104.

The tubular access sleeve 10 and suction tool 30 or the present invention are employed to access the pericardium 106 and to grip its surface to tension it so that an incision can be made through the pericardium 106 to access the pericardial space and epicardium of the heart 104. The elongated access sleeve 10 provides an working lumen 18 enabling introduction of a cutting instrument 80, e.g., a knife, a needle, a stiff guidewire tip, an electrosurgical cutting tool, surgical scissors, or other piercing or cutting instrument, to first perforate the pericardium 106 and then form an access hole or perforation 114 exposing the pericardial space and exterior surface of the epicardium of the heart 104.

The tubular access sleeve 10 of the present invention incorporates or accommodates a suction tool 30 comprising at least two suction pads at the ends of at least two elongated arms that can be retracted into the tubular access sleeve 10 during introduction and advancement of the tubular access sleeve distal end into operative relation to the pericardium 106 and deployed out of the tubular access sleeve 10 and disposed against the pericardium 106. Suction can be applied through suction tool lumens of the suction tool 30 from a vacuum source to suction ports of the suction pads that fix to the pericardium 106 so as to tension it and/or pull it away from the epicardium and/or stabilize the pericardium 106 and/or track any movements of the pericardium. Suction is applied to suction tool lumens of the suction tool 30 through a hose 72 and fitting 70 that can be grasped to move the suction tool 30 distally until the fitting contacts the tubular access sleeve proximal end or proximally with respect to the tubular access sleeve 10.

The tubular access sleeve 10 depicted in FIGS. 2 and 3 is formed of a thin-wall sleeve body 12 enclosing the working lumen 18 and a suction tool lumen 22 separated by lumen wall 20. The working lumen 18 extends from a working lumen proximal end opening at the sleeve body proximal end 14 to a working lumen distal end opening at the sleeve body distal end 16. The lumen wall 20 extends from the sleeve body proximal end to a lumen wall distal end 21 proximal to the sleeve body distal end 16, so that the suction tool lumen 22 extends from a suction tool lumen proximal end opening at the sleeve body proximal end 14 to a suction tool lumen distal end opening at the lumen wall distal end 21.

It will be understood that the working lumen 18 and the suction tool lumen 22 are sealed to prevent loss of pressurization of the working space within the patient's thoracic cavity during the procedure. Thin, penetrable seals of flexible material, e.g., silicone rubber can be formed extending across the working lumen 18 and the suction tool lumen 22 or a bitumen hub can be attached to the access sleeve proximal end 14 providing the seals and access to the working lumen 18 and the suction tool lumen 22.

Figure 4:
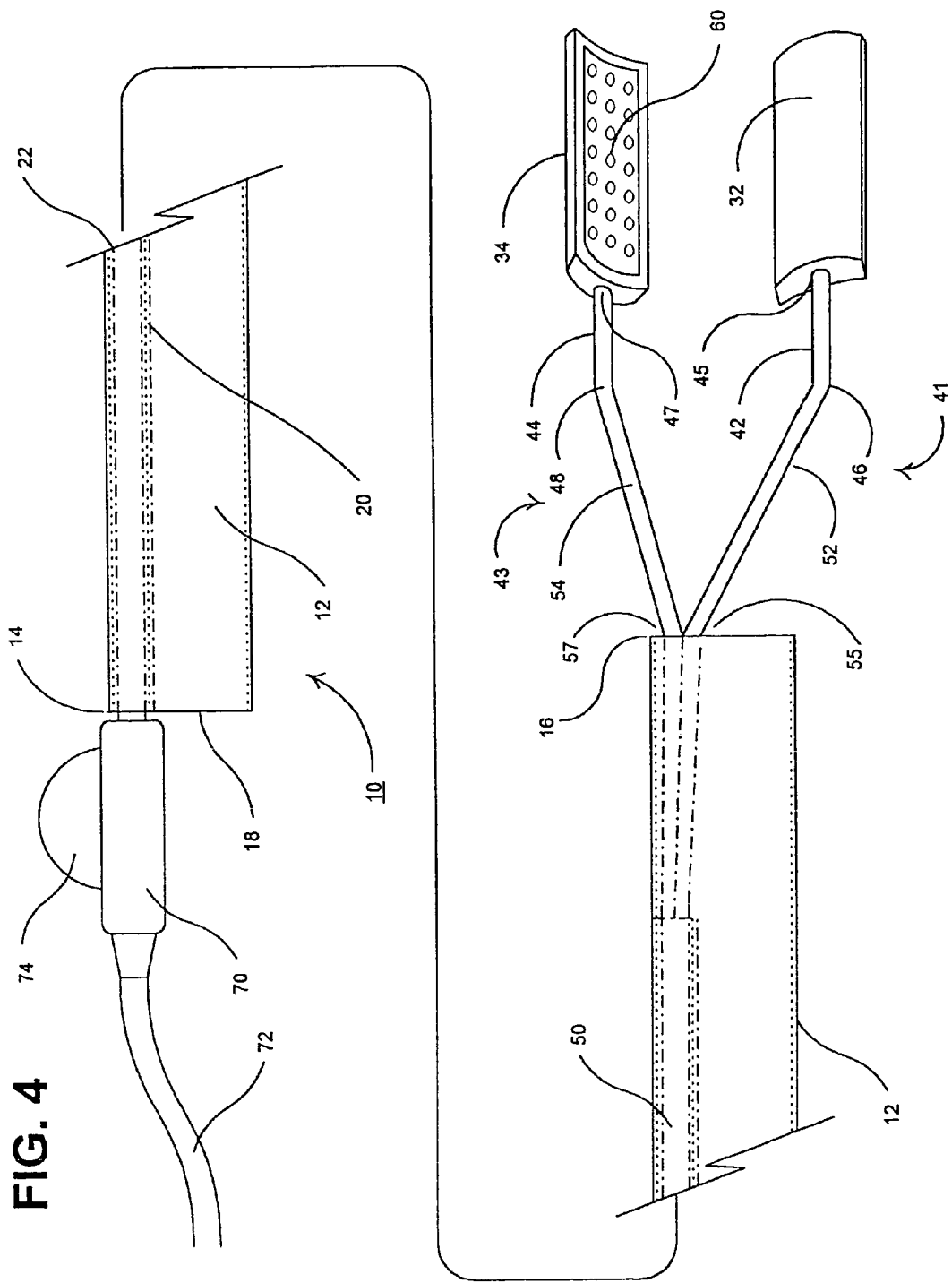
FIG. 4 is a side view of the tubular access sleeve of FIG. 2 loaded with a suction tool of the present invention with the suction pads deployed from the working lumen of the access sleeve.

In a preferred embodiment depicted in FIG. 4, the suction tool 30 comprises a pair of elongated support arms 41 and 43 that support elongated suction pads 32 and 34, respectively. A plurality of suction ports 60 are formed in an array through tissue contacting surfaces of the suction pads 32 and 34. The suction ports 60 are coupled through a suction manifold within the suction pads 32 and 34 to suction tool lumens of the support arms 41 and 43. Suction applied through the suction ports 60 grasps tissue, e.g., the exterior pericardial surface. The suction pads 32 and 34 are coupled to the distal end of the support arms 41 and 43, respectively, through flexible wrists 45 and 47, respectively. The support arms 41 and 43 comprise distal forearms 42 and 44, respectively, extending from the flexible wrists 45 and 47, respectively, to flexible elbows 46 and 48, respectively. Proximal upper arms 52 and 54 extend from the elbows 46 and 48, respectively, to flexible shoulder joints 55 and 57, respectively, with a common proximal suction tool trunk 50. The proximal suction tool trunk 50 extends proximally through the suction tool lumen 22 of the tubular access sleeve 10 out of the proximal end opening or the suction tool lumen to the fitting 70.

Figure 8:
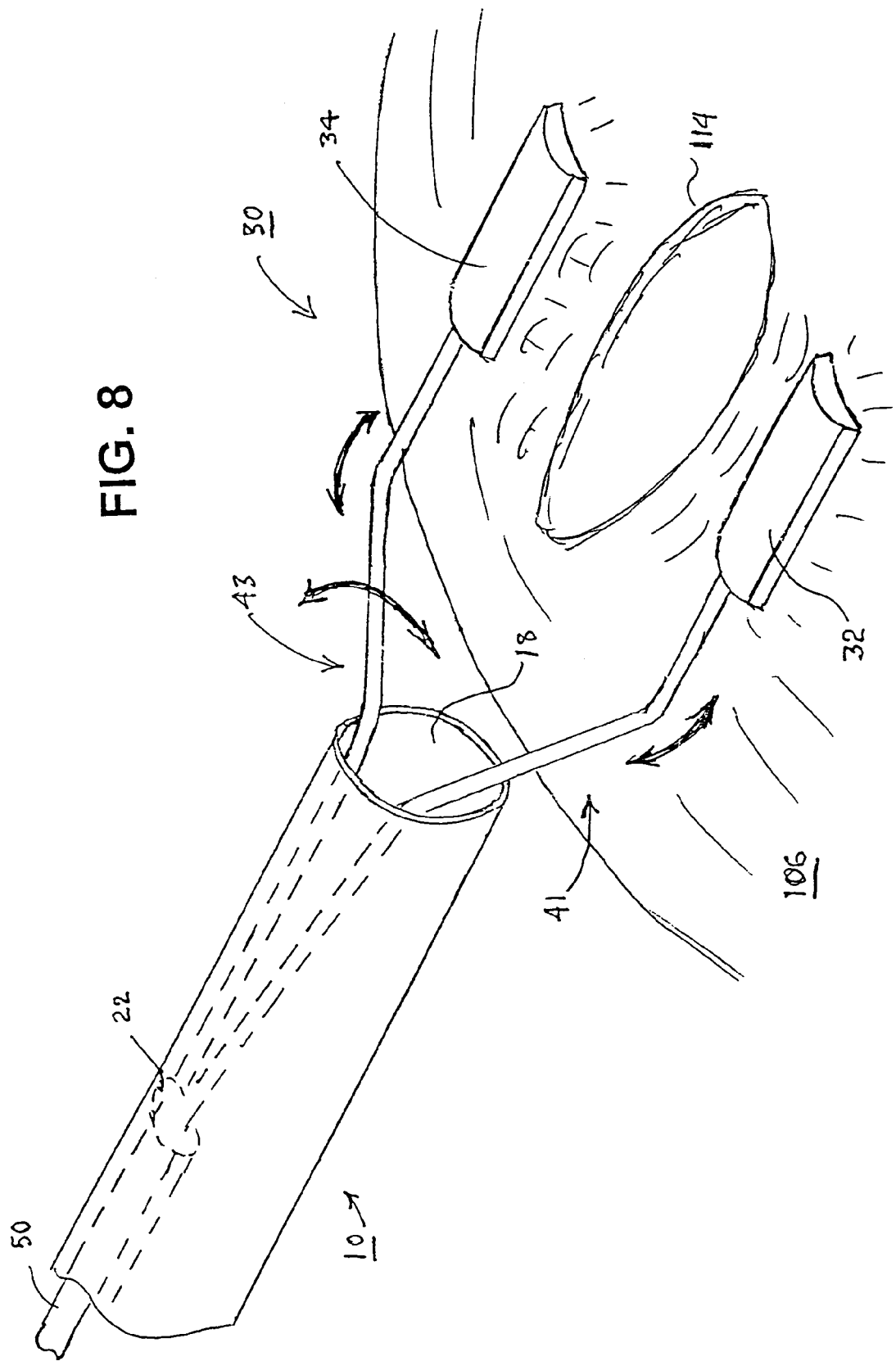
FIG. 8 is a perspective view of the distal segment of the tubular access sleeve of FIG. 2 with the suction pads of the suction tool of FIG. 4 deployed from the working lumen of the access sleeve against the pericardium and a hole formed through the pericardium.

Each support arm 41, 43 is formed of a flexible tube, preferably a thin-walled polymeric tube, that has preformed bends at the wrist 45, 47, elbow 46, 48 and shoulder joint 55, 57, that, when unrestrained, dispose the suction pads 32 and 34 apart from one another and at an angle to the longitudinal axis of the access sleeve 10 as shown in FIGS. 4 and 8. The proximal suction tool trunk 50 can comprise proximal extensions of the flexible tubes forming the support arms 41 and 43 extending from the shoulder joints 55 and 57 to the distal side of the fitting 70 that are either joined together or retained side-by-side by the suction tool lumen 22. The proximal trunk 50 can comprise a thin-wall tube having a tube lumen through which the proximal extensions of the flexible tubes forming the support arms 41 and 43 extend. Or, the proximal extensions of the flexible tubes forming the support arms 41 and 43 can be joined together side-by-side either by co-extrusion of the flexible tubes or by adhesive.

As shown in FIGS. 4 and 8, the suction pads 32 and 34 are disposed a distance apart by the preformed bends so that the suction pads 32 and 34 can cooperatively grasp the outer surface of the pericardium 106 (or other outer tissue layer) at separated apart locations so that the outer surface between the suction pads 32 and 34 can be operatively accessed through the working lumen 18. (The suction pad 34 is rotated out of its normal disposition in FIG. 4 to depict the array of suction pads 60.)

The preformed bends at the wrists 45 and 47, elbows 46 and 48 and shoulder joints 55 and 57 can be overcome to dispose the arms 41 and 43 parallel to one another when drawn proximally into the suction tool lumen 22. As shown in FIGS. 5–7, the trunk 50 and support arms 41 and 43 can be drawn proximally into the suction tool lumen 22 to dispose the suction pads 32 within a distal portion of the working lumen 18 during surgical insertion or withdrawal of the tubular access sleeve 10 from the patient's body 100. The elongated suction pads 32 and 34 are drawn together and aligned axially with the working lumen 18 so that the suction pads 32 can be drawn into the distal segment of the working lumen 18.

Once the sleeve body distal end 16 is disposed at the desired site of the pericardium (or other outer tissue layer), the trunk 50 and support arms 41 and 43 can be advanced distally through the suction tool lumen 22 to extend the support arms 41 and 43 and suction pads 32 and 34 from the distal end opening of the working lumen 18. The radial angle of advancement with respect to the working lumen 18 can be gauged by the relation of the tab 74 with a marking or markings along the sleeve body proximal end 14. The suction pads 32 and 34 grasp the outer surface of the pericardium when suction is applied through the suction ports 60. The deployment and application of the suction pads 32 and 34 to the external surface of the pericardium 106 is depicted in FIG. 8.

Due to their redundancy, the plurality of suction ports 60 of the suction pads 32 and 34 provide more robust fixation to the pericardium 106 (or other outer tissue layer) than a single large area suction port. At least some of the suction ports 60 readily engage the pericardial surface under low suction force to enable lifting and spreading laterally of the pericardium 106 or tracking movement of the pericardium 106. Engagement of the surface of the pericardium 106 by all of the suction ports 60 is not necessary. Similarly, the loss of engagement of some of suction ports 60 with the surface areas of the pericardium 106 does not result in complete loss of engagement as is the case when an edge of a single large suction port releases from a tissue surface of an outer tissue layer.

Initially, the trunk 50 and support arms 41 and 43 can be advanced distally through the suction tool lumen 22 to partially extend the support arms 41 and 43 and suction pads 32 and 34 from the distal end opening of the working lumen 18 against the surface of the pericardium 106. Suction is applied so that the suction pads grasp the surface of the pericardium 106. The cutting instrument or tool can then be introduced through the working lumen 18 to perforate and cut the pericardium 106 (or other outer tissue layer) and form the access hole 114 therethrough. The trunk 50 and support arms 41 and 43 are then advanced distally through the suction tool lumen 22 to fully extend the support arms 41 and 43 and suction pads 32 and 34 from the distal end opening of the working lumen 18 suction pads and to spread the hole 114 through pericardium 106.

Advantageously, there is no suction applied through the working lumen 18 that is necessary to maintain the attachment to the pericardium 106 while it is being cut to form the access hole 114 to the pericardial space so that other instruments are advanced through the hole 114.

In this way, methods, apparatus and kits of the present invention can advantageously be used to access the pericardial space between the pericardium and epicardium. Various devices can be introduced into the pericardial space through the access lumen 18 for temporary treatment of the heart or pericardial space or to complete a surgical procedure or for permanent implantation against the epicardium or within the pericardial space or within the myocardium or within a coronary vein or artery.

The tubular access sleeve 10 can be circular or oval or have any other desirable cross-section shape. The tubular access sleeve 10 can be straight, curved for formed with a bend or formed of a bendable material to be shaped by the user.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A method of accessing an anatomic space of a patient comprising:
    advancing a tubular access sleeve having a working lumen and a suction tool lumen through an opening in the patient to dispose a distal end of the sleeve adjacent tissue enclosing the anatomic space;
    advancing a suction tool comprising a suction pad mounted to a support arm branching from a suction tool trunk and suction ports through the suction tool lumen to extend the suction ports distally from the sleeve, the suction pad comprising at least a portion of the suction ports; and
    applying suction through the suction ports to grasp the tissue, whereby the anatomic space may be accessed through the working lumen.

2. The method of claim 1 further comprising the step of advancing a cutting tool through the working lumen and cutting through the tissue while suction is applied through the suction ports to grasp the tissue.

3. The method of claim 1 wherein the suction tool further comprises a second suction pad mounted to a second support arm branching from the suction tool trunk, the second suction pad comprising at least a portion of the suction ports.

4. The method of claim 3 further comprising:
    advancing a cutting tool through the working lumen;
    creating an incision in the tissue while suction is applied through the suction ports of the suction pads to grasp the tissue; and
    moving the suction pads apart to tension the tissue and widen the incision, whereby the anatomic space may be accessed through the incision.

5. The method of claim 1 wherein the step of advancing a tubular access sleeve includes the step of disposing the distal end of the sleeve adjacent pericardial tissue.

6. The method of claim 1 including the step of making a subxiphoid opening and advancing the tubular access sleeve through the subxiphoid opening.

7. The method of claim 1 including the step of making an intercostal opening and advancing the tubular access sleeve through the intercostal opening.

8. The method of claim 1 including the step of making a transthoracic opening and advancing the tubular access sleeve through the transthoracic opening.

9. The method of claim 1 further comprising the step of advancing a medical device through the working lumen, wherein the medical device is selected from the group consisting of an electrosurgical tool, a thoracoscope, an endoscope, a lead, an electrode, a catheter, a guidewire and a cutting instrument.

10. The method of claim 1 further comprising the step of delivering a drug through the working lumen to the anatomic space.

11. The method of claim 1 further comprising the step of delivering a diagnostic agent through the working lumen to the anatomic space.

12. A system for accessing an anatomic space of a patient comprising:
    a tubular access sleeve having a working lumen and a suction tool lumen; and
    a suction tool disposed within the suction tool lumen comprising a suction pad coupled to a support arm extending distally from a tool trunk and suction ports, wherein the suction pad comprises at least a portion of the suction ports, the suction ports being deployable distally from the sleeve.

13. The system of claim 12 wherein the suction tool further comprises a second suction pad coupled to a second support arm extending distally from the tool trunk, the second suction pad comprising at least a portion of the suction ports.

14. The system of claim 13 wherein the suction tool further comprises a suction lumen extending from the suction pads through the support arms and through the suction tool trunk to a proximal end of the trunk.

15. The system of claim 14 further comprising a suction fitting at the trunk proximal end communicating with the suction lumen, the suction fitting being capable of being coupled to an available surgical operating room vacuum source.

16. The system of claim 12 wherein the suction ports are housed within the working lumen by proximal retraction of the suction tool trunk and are deployable distally from the working lumen upon distal advancement of the suction tool trunk within the suction tool lumen.

\* \* \* \* \*